(12) United States Patent
Xu et al.

(10) Patent No.: US 8,487,119 B2
(45) Date of Patent: Jul. 16, 2013

(54) ORGANIC SENSITIZERS

(75) Inventors: Mingfei Xu, Changchun (CN); Hao Qin, Changchun (CN); Feifei Gao, Changchun (CN); Peng Wang, Changchun (CN); Shaik Mohammad Zakeeruddin, Bussigny (CH); Michael Graetzel, St-Sulpice (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 189 days.

(21) Appl. No.: 12/735,629

(22) PCT Filed: Feb. 3, 2009

(86) PCT No.: PCT/IB2009/050441
§ 371 (c)(1),
(2), (4) Date: Nov. 4, 2010

(87) PCT Pub. No.: WO2009/098643
PCT Pub. Date: Aug. 13, 2009

(65) Prior Publication Data
US 2011/0041907 A1 Feb. 24, 2011

(30) Foreign Application Priority Data
Feb. 4, 2008 (CN) .................. 2008 1 0050371

(51) Int. Cl.
*H01L 31/00* (2006.01)
*C07D 495/02* (2006.01)

(52) U.S. Cl.
USPC ............................................ 549/43; 549/50

(58) Field of Classification Search
None
See application file for complete search history.

(56) References Cited

U.S. PATENT DOCUMENTS
2009/0044857 A1* 2/2009 Shigaki et al. ................ 136/256

FOREIGN PATENT DOCUMENTS
EP          1 628 356        2/2006
WO   WO 2007/100033    *  9/2007

OTHER PUBLICATIONS

Qin; An Organic Sensitizer with a Fused Dithienothiophene Unit for Efficient and Stable Dye-Sensitized Solar Cells; J. Am. Chem. Soc., vol. 130, No. 29, Jun. 27, 2008, pp. 9202-9203JACS, XP002569724, p. 9202, figure 1.

* cited by examiner

*Primary Examiner* — Noble Jarrell
*Assistant Examiner* — Valerie Rodriguez-Garcia
(74) *Attorney, Agent, or Firm* — Kreig DeVault LLP; Clifford W. Browning

(57) ABSTRACT

The present invention relates to new organic sensitizer compounds and to photoelectric conversion devices, in particular dye-sensitised solar cells comprising the new sensitizers. The present invention also relates to flexible photoelectric conversion devices, which are based on ionic liquid electrolytes or organic charge transporting materials.

18 Claims, 2 Drawing Sheets

ORGANIC SENSITIZERS

This application claims the benefits under 35 U.S.C. 119 (a)-(d) or (b), or 365(b) of International Application No. PCT/IB2009/050441 filed 3 Feb. 2009, and China Patent Application No. 200810050371.5, filed 4 Feb. 2008.

TECHNICAL FIELD

The present invention relates to the field of photoelectric conversion devices, in particular photovoltaic cells. More particularly, the present invention relates to conversion devices comprising sensitising compounds, in particular sensitising dyes.

PRIOR ART AND THE PROBLEM UNDERLYING THE INVENTION

The use of conventional fossil fuels as energy resource poses well-known environmental problems, as well as problems of shortage in the medium to long term. In order to solve the approaching energy crisis, a variety of attempts have been performed. Among the available alternatives, the solar energy, used in photovoltaic cells, is almost unlimited and environment-friendly compared to other forms of energy. The silicon solar cell dominates the photovoltaic business due to the high light-to-electricity conversion efficiency and due to the fact that the technology developed for many decades, is mature. However, silicon solar cells suffer from the disadvantages of a high cost of the production process, expensive raw materials and the difficulty of further increasing the efficiency of the cells.

Dye sensitised solar cells (DSCs) make use of photosensitive dye molecules (sensitizers) and transition metal oxides, which perform the functions of absorbing visible light, producing electron—hole couples, and transporting the electron produced by light absorption, respectively. DSCs have many advantages, such as high efficiency, low production cost, low energy consumption during manufacturing, and environmental friendly production. These properties have given these cells high prospects in the photovoltaic business. In 1991, Prof. Michael Grätzel at the École Polytechnique Fédérale de Lausanne developed a technological breakthrough in these cells. Since then, DSCs have gradually become a research topic of high interest in the field of solar cells (Nature 1991, 353, 737). So far, DSCs with high efficiency usually use sensitizers containing a noble metal, as is the case in bipyridine ruthenium complexes, for example (J. Am. Chem. Soc. 2005,127, 16835-16847). However, the practical application of such complexes is limited by the high price of noble metals and their limited resource. Compared to bipyridine ruthenium complex, organic dyes show some advantages, such as low cost, high extinction coefficient and the possibility of modifying the structure easily. Recently, in the field of DSCCs, efforts have been made for replacing ruthenium dyes with organic dyes (J. Am. Chem. Soc. 2006, 128, 16701-16707).

In particular, the present invention addresses the objectives of providing new dyes with low production cost, and high stability, resulting in photovoltaic conversion devices having improved characteristics, such as a high energy conversion efficiency.

Furthermore, flexible solar cells have been proposed, which are generally light in weight and thus enjoy the advantage of easy transportation in practical application as electricity sources, for example for lap-top computers, mobile phones, and watches. Furthermore, replacing a rigid substrate by a flexible material allows a low-cost fabrication by roll-to-roll mass production. Therefore, applying flexible-device technologies to dye-sensitized solar cells, a prospective cost effective photovoltaic-generating system, is very significant, as is proposed by Seigo Ito et al., "High-efficiency (7.2%) flexible dye-sensitized solar cells with Ti-metal substrate for nanocrystalline-$TiO_2$ photoanode" (Chem. Commun. 2006, 4004-4006). However, these devices suffer from poor stability. The present inventors determined that part of the poor stability could be explained by the evaporation of solvents used in electrolytes of such devices through the flexible plastic substrates. Unfortunately, this problem is also found when solvents with high boiling points, such as 100° C. or higher, or even 150° C. or higher are used. It is thus an objective of the present invention to produce more stable flexible solar cells. It is another objective to produce a device being prepared to an increasing extent from plastic and/or organic materials. In particular, it is an objective to produce a flexible solar cell avoiding the problem of electrolyte degradation due to solvent evaporation and at the same time reducing and/or completely avoiding the use of noble metals such as ruthenium in sensitizer compounds.

The present invention addresses the problems depicted above.

SUMMARY OF INVENTION

The present invention provides organic compounds, which can be used as sensitizer dyes in dye-sensitized photoelectric conversion devices. Dye sensitized solar cells comprising the organic dyes shows more than 90% light-to-electricity conversion efficiency and higher than 10% cell efficiency. With these characteristics, the organic dyes are the most efficient organic sensitizers in the world so far. The efficiency of dye-sensitized solar cells with the organic dyes is very close to that of corresponding cells using noble metal complexes as sensitizers. The said dyes have a promising prospect in dye sensitised photoelectric conversion devices.

Furthermore, the present inventors provide a flexible solar cell, which does not suffer from the stability problems as prior art devices. According to an embodiment, sensitizer compounds used in these flexible comprise or consist of organic dyes in combination with solvent free ionic liquid based electrolytes.

In a first aspect, the present invention relates to a photoelectric conversion device, in particular to a dye-sensitized conversion device.

Accordingly, the present invention provides, in an aspect, an organic dye of formula (1):

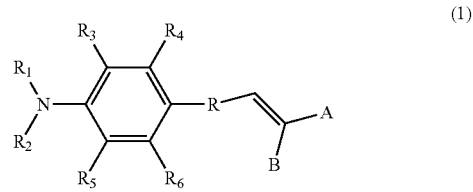

wherein:

$R_1$, $R_2$, $R_3$, $R_4$, $R_5$ and $R_6$ are, independently one from the other, selected from a hydrogen atom (H), alkyl, alkoxyl, aromatic hydrocarbons, or heterocycles and derivatives these, wherein said alkyl, alkoxyl, aromatic hydrocarbon or heterocycle may be substituted or unsubstituted and may contain one or more heteroatoms, and wherein one or more of $R_3$, $R_4$, $R_5$ and $R_6$ may also be selected from halogen;
R comprises or preferably consists of one or up to ten identical or different successive moieties, which is/are selected independently one from the other from the moieties represented in formulae (2) to (21) below:
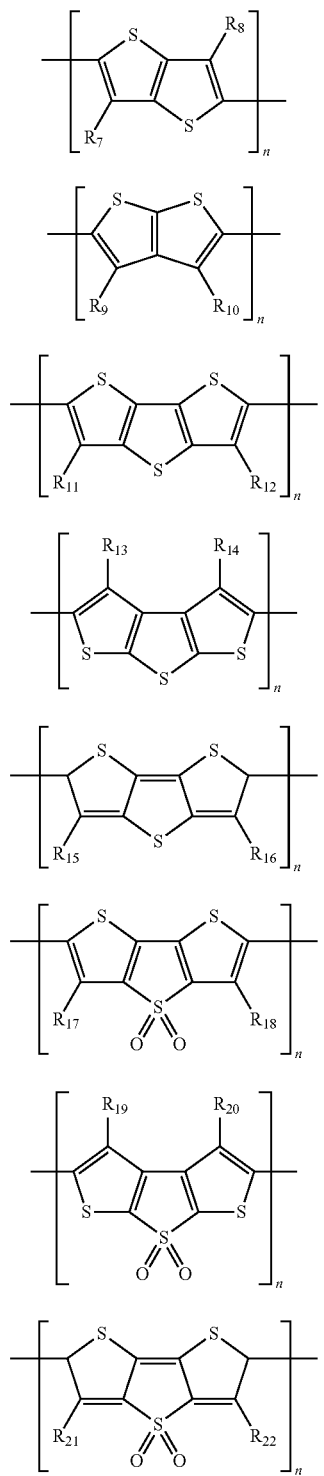
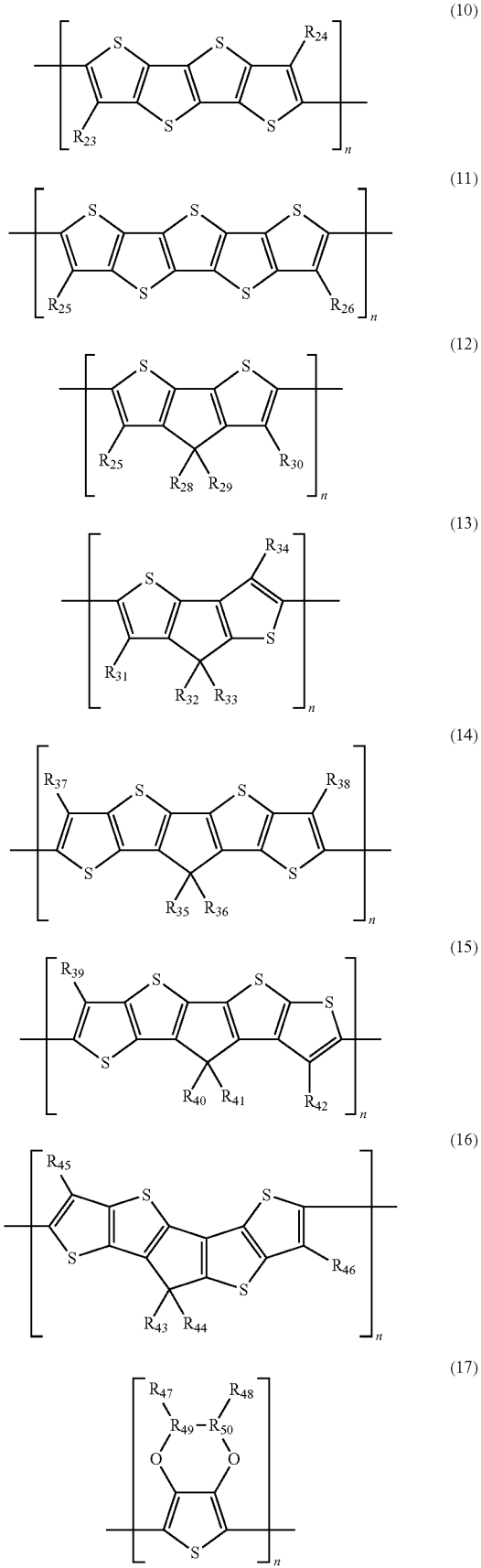

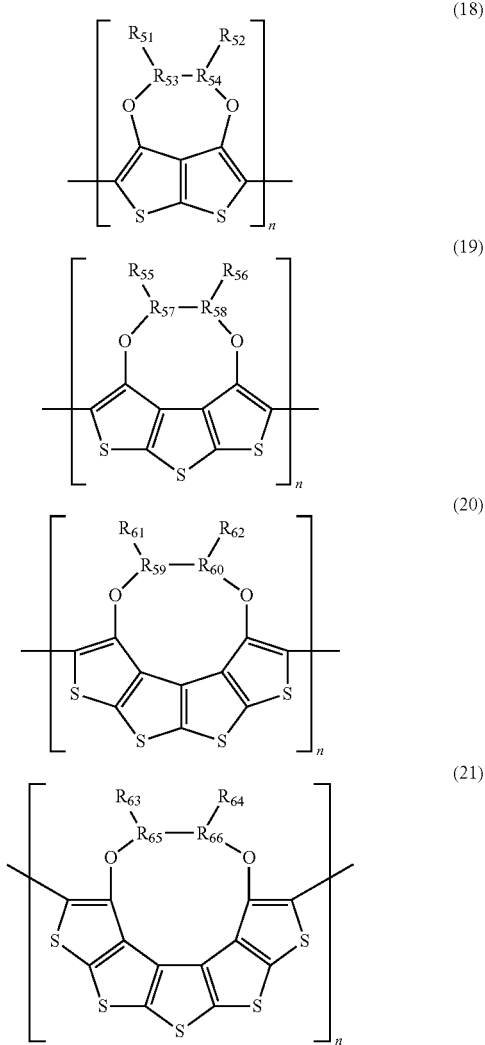

(18), (19), (20), (21)

wherein:
n is an integer selected from 1-10, and is preferably 1, 2, or 3;
$R_{49}$, $R_{50}$, $R_{53}$, $R_{54}$, $R_{57}$, $R_{58}$, $R_{59}$, $R_{60}$, $R_{65}$, $R_{66}$ are generally carbon (the hydrogen attached to the carbon is not shown);
$R_7$ to $R_{66}$, with the exception of $R_{49}$, $R_{50}$, $R_{53}$, $R_{54}$, $R_{57}$, $R_{58}$, $R_{59}$, $R_{60}$, $R_{65}$, $R_{66}$, are selected, independently one from the others, from H, hydroxyl, nitryl, amido, acyl, alkyl, cycloalkyl, alkoxyl, aromatic hydrocarbons and their derivatives, alkylsulfonyl, alkylthio, ester group, alkyl halide, halogen, sulfonyl, cyano, alkenyl, acyloxyl, carboxyl and heterocycles;
A in the compound of formula (1) is an acceptor group selected cyano, acyl, aldehyde group, carboxyl, acylamino, sulfonic, nitryl, haloform and quaternary ammonium;
B is selected carboxyl, phosphorus acid, sulfonic acid, hypophosphorous acid, hydroxyl, oxidation carboxylic acid, acylamide, boric acid, and squaric acid, including deprotonated forms of the aforementioned.

In another aspect, the present invention provides photovoltaic conversion device, in particular a dye-sensitised solar cell (DSC) comprising an organic dye according to the invention, and to the use of compounds as disclosed herein as sensitizers in dye-sensitizer photovoltaic conversion devices.

In an aspect, the present invention relates to a flexible, dye-sensitized photoelectric conversion device comprising, between a dye-layer and a counter electrode, an electrically conductive, charge transport material and/or electrolyte layer, wherein said charge transport and/or said electrolyte layer are solvent-free.

Further aspects and preferred embodiments of the present invention are detailed in the appended claims.

DETAILED DESCRIPTION OF THE PREFERRED EMBODIMENTS

Figure 1:
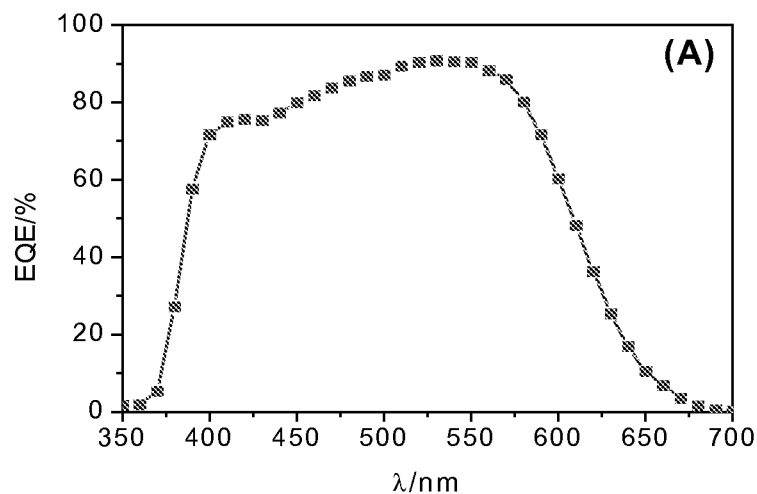
FIG. 1 shows the photocurrent action spectrum of a dye-sensitised solar cell sensitized with dye represented by formula (1) according to the invention.
Figure 2:
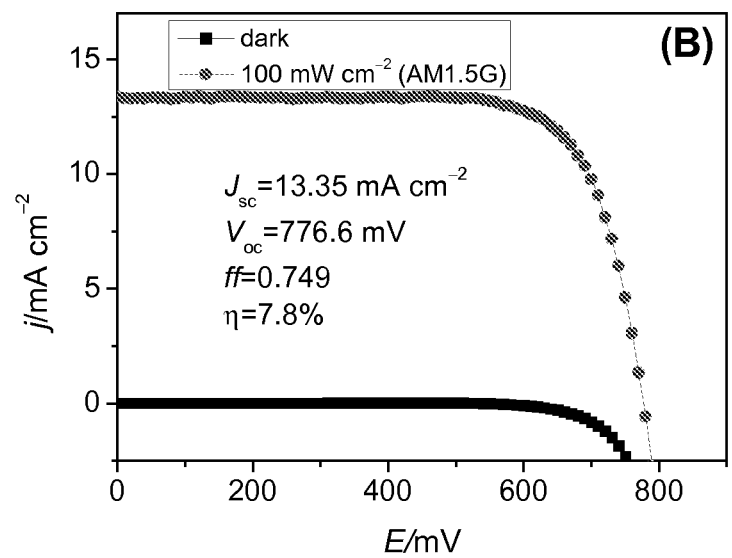
FIG. 2 shows the current density-voltage characteristics of a DSC with the dye represented by formula (1) under illumination of the AM 1.5G full sunlight (100 mW cm$^{-2}$) and in dark according to the invention.

The present invention relates to photoelectric conversion devices. The photoelectric conversion device is preferably a photovoltaic cell, in particular a solar cell, capable of converting electromagnetic radiation, in particular visible, infrared and/or UV light, in particular sunlight, into electrical current. According to a preferred embodiment, the photoelectric conversion device is a dye-sensitized conversion device, in particular a dye-sensitized solar cell (DSC). The terms "dye", "sensitizer", "sensitising dye" and "dye sensitizer" all encompass the respective other terms and are considered as synonyms.

The present invention relates in particular to compounds that are useful as sensitizers in photoelectric conversion devices. In an embodiment, $R_1$ and $R_2$ of formula (1) above are selected from substituted and unsubstituted aryls, wherein said aryl and/or one or more of said optional substituents may comprise one or more heteroatoms.

According to an embodiment, said aryl is a substituted or unsubstituted phenyl, biphenyl, or an aromatic system of condensed cycles, which may be substituted or unsubstituted.

If said $R_1$ and $R_2$ are substituted aryls, said substituents of said aryl may be selected, for example, from alkyl, alkoxyl, aryl, arylated alkyl, arylated alkoxyl, alkylated aryl, and alkoxylated aryl, polyether, all of which may comprise one or more heteroatoms, in addition to the one or more heteroatom present by definition in some of the named substituents.

For example, the aryl of $R_1$ and $R_2$ may be a condensed ring system, such as for example the condensed system fluoren, this condensed ring system may comprise one or more alkyl substituents, as is the case in 9,9-dimethlyfluoren-2-yl, which are a preferred embodiment of $R_1$ and $R_2$. Said alkyl substituent may comprise one or more heteroatoms. Other preferred embodiments encompass substituted and unsubstituted phenyls, for example alkyl, alkoxyl-substituted and/or polyether-substituted phenyls.

According to an embodiment, each substituent $R_1$ and $R_2$ of formula (1) may have 6-40, preferably 10-25 carbons, and 0-20, preferably 0-10 heteroatoms.

Preferably, $R_1$ and $R_2$ are selected from substituted and unsubstituted aryls. Preferably, the aryl has 10-25 carbons and 0-5 heteroatoms, and each substituent, if present, has 1-15 carbons and 0-5 heteroatoms.

Preferred heteroatoms optionally comprises in $R_1$ and/or $R_2$ are one or more selected from halogen, N, O, P, S.

In R of the compounds of formula (1), n is an integer selected from 1-10, but is preferably selected from 1, 2 or 3, meaning that up to three identical moieties may succeed each other.

Alternatively, any moiety of R selected from the moieties (2)-(21), may succeed a different moiety, as is illustrated, for example, with compound (X) further below, where there are three different moieties, namely moiety (17) (with $R_{55}$ and $R_{56}$ being H), followed by moieties (2) and (4). It is also possible that a specific moiety selected from the moieties (2)-(21) recurs twice or even more times, such as with compound (IX) below, where moieties 1 and 3, when starting from the triphenylamine, are the same.

In general, in the compound of formula (1), R represents from 1-10, preferably 1-3 moieties, said moieties being independently selected from the moieties of formulae (1)-(21). In other words, any combination of the moieties (2)-(21) may be used.

In the moieties of formulae (17)-(21), $R_{49}$, $R_{50}$, $R_{53}$, $R_{54}$, $R_{57}$, $R_{58}$, $R_{59}$, $R_{60}$, $R_{65}$, $R_{66}$ represent in general carbon. The hydrogen for making up the complete valence of the carbon was not shown. A halogen can be present in the place of hydrogen at this carbon. Other atoms could be used at the position of $R_{49}$, $R_{50}$, $R_{53}$, $R_{54}$, $R_{57}$, $R_{58}$, $R_{59}$, $R_{60}$, $R_{65}$, $R_{66}$, but, as the skilled person will understand, this then depends of the nature of the further substituents (for example, in moiety (21), of substituents $R_{63}$ and $R_{64}$), and also of the connection between these moieties (for example, it is clear that $R_{65}$ and $R_{66}$ could not both be oxygen).

The amido, acyl, alkyl, cycloalkyl, alkoxyl, aromatic hydrocarbons and their derivatives, alkylsulfonyl, alkylthio, ester group, alkyl halide, halogen, sulfonyl, alkenyl, acyloxyl, carboxyl and heterocyclic substituents, which may be used in the position of $R_7$ to $R_{66}$ (with the exception of $R_{49}$, $R_{50}$, $R_{53}$, $R_{54}$, $R_{57}$, $R_{58}$, $R_{59}$, $R_{60}$, $R_{65}$, $R_{66}$) as mentioned above, preferably comprise 1-50, more preferably 1-20 and most preferably 1-10 carbons, and heteroatoms are provided at least as necessary to form the respective substituent (for example, acyl requires, of course, an oxo group, and thus an oxygen heteroatom).

According to a preferred embodiment, the organic dye is selected from a compound of any one of formula (I) to (X) below:

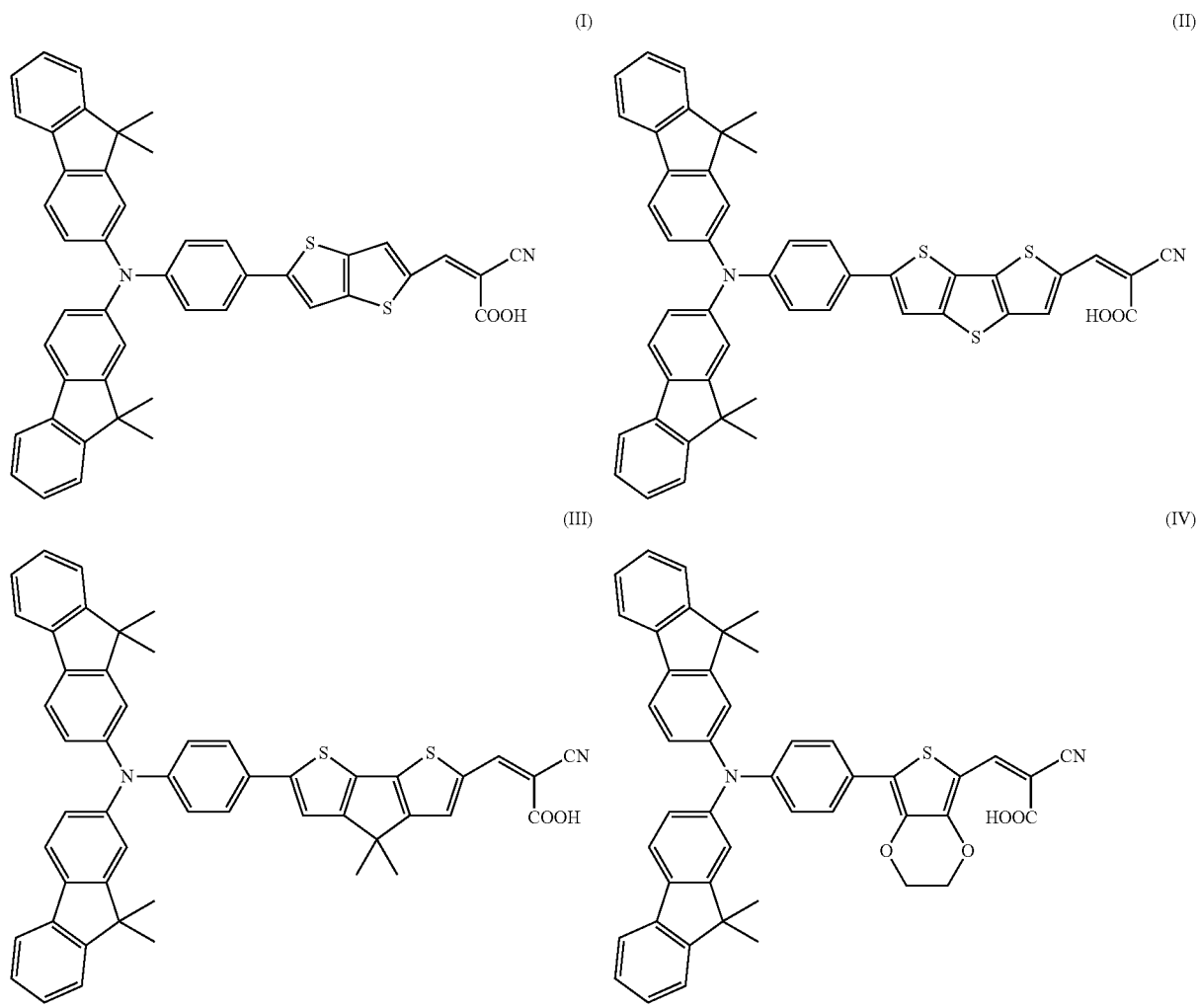

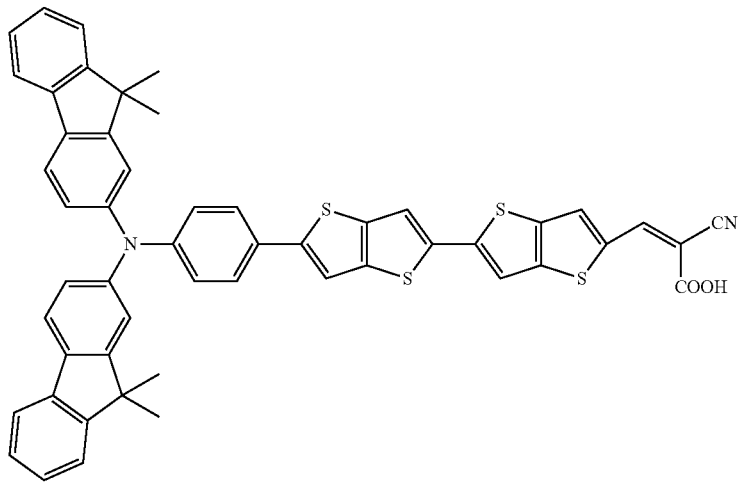
(V)
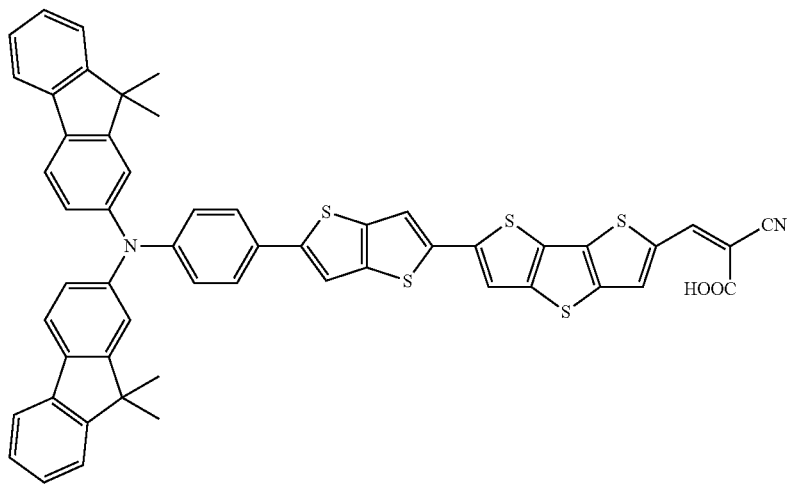
(VI)
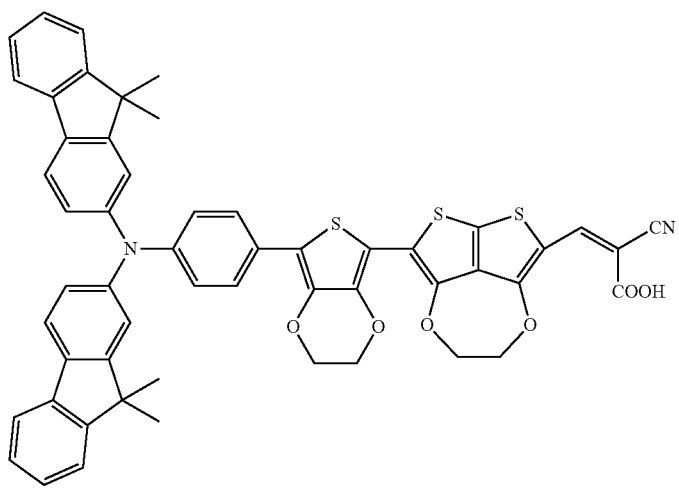
(VII)

(VIII)

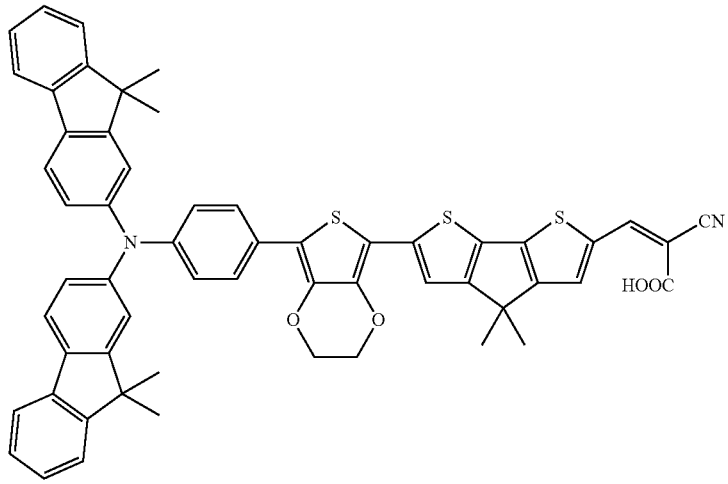

(IX)

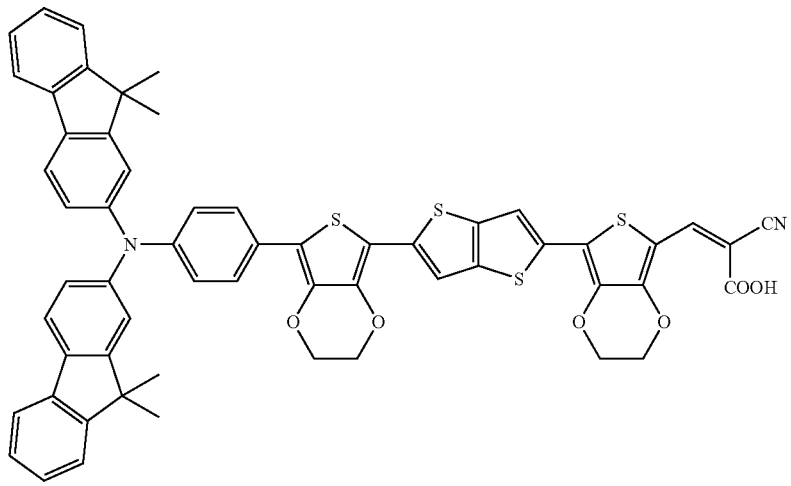

(X)

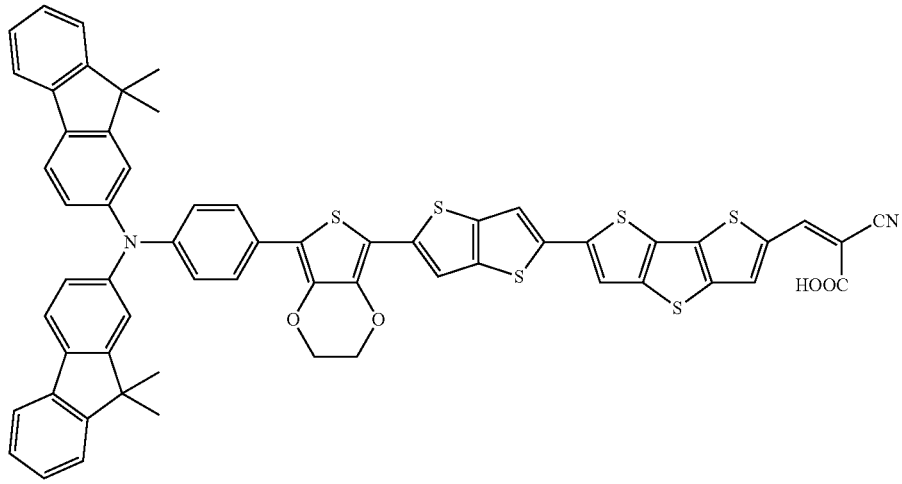

The present invention also relates to photoelectric conversion devices, in particular solar cells. For the purpose of illustration, the present invention is explained at the embodiments of such devices shown in FIGS. 3-5. The device shown in FIG. 3 can also be considered as a flexible device.

The device of the present invention comprises at least one substrate 1. Contrary to the device shown in FIG. 3, the present invention also encompasses devices having only one substrate 1, for example only a top or only a bottom substrate 1, as is shown more specifically in FIG. 5. Preferably, there is a substrate facing the side of the device intended to be exposed to electromagnetic radiation for production of electrical current. The substrate facing radiation is preferably transparent. Transparency, for the purpose of the present invention, generally means that the respective structure (for example substrate, counter electrode, conductive layer, porous semiconductor) is transparent to at least some visible light, infrared light or UV light, in order to convert this light to electrical energy in the device of the invention. Preferably, transparent means transparent to all visible light, more preferably also to some of the near infra-red and/or also to at least part of the ultraviolet light spectrum.

The substrate 1 may be made from plastic or from glass. In flexible devices, the substrate 1 is preferably made from plastic. In an embodiment, the substrate comprises a plastic selected from the groups of polyethylene terephthalate, polyethylene naphthalate, polycarbonate, polypropylene, polyimide, 3-acetyl cellulose, and polyethersulfone, for example.

Figure 5:
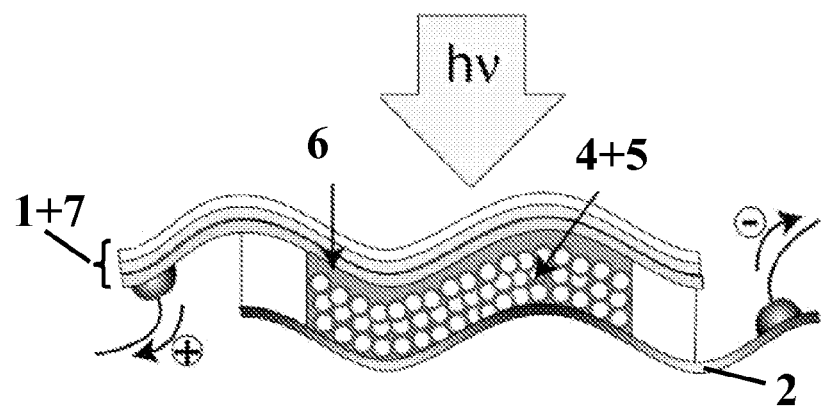
FIG. 5 is a schematic representation of an embodiment of a flexible conversion device of the present invention, which is irradiated through the counter electrode (back illumination).

The conversion devices of the present invention generally have two conductive layers 2 and 7, wherein a first conductive layer 2 is required for removing the electrons generated from the device, and a second conductive layer 7 for supplying new electrons, or, in other words, removing holes. This is illustrated in FIG. 5 by the signs + and −. The conductive layers 2 and 7 may be provided in many different forms and may be made from various materials, depending on the purpose or nature of the device.

The second conductive layer 7 is generally part of the counter electrode 7 and is already part of the substrate, as is the case, for example with ITO (indium tin oxide)-coated plastic or glass, where the transparent ITO is coated on the plastic or glass and makes the later electrically conductive.

Accordingly, one or both conductive layers 2 and 7 may comprise a transparent metal oxide, such as indium doped tin oxide (ITO), fluorine doped tinoxide (FTO), $ZnO—Ga_2O_3$, $ZnO—Al_2O_3$, tin-oxide, antimony doped tin oxide (ATO) and zinc oxide.

According to embodiments of the invention, only the first conductive layer 2 or only the second conductive layer 7 comprises a transparent metal oxide layer as defined above. It is also possible to provide one or both of the two opposed conductive layers 2 and 7 in the form of a conductive foil, for example a metal foil, in particular a titanium foil or zinc foil. This is preferred, for example, in some flexible devices, as detailed below. Preferably, the first conductive layer 2, is made from a conductive metal foil, for example, as is shown in FIG. 5. Such a foil may not be transparent.

The device of the present invention generally comprises a counter electrode 7, which faces an intermediate layer 6 towards the inside of the cell, and the substrate 1 on the outside of the cell, if such substrate is present. The counter electrode generally comprises a catalytically active material, suitable to provide electrons and/or fill holes towards the inside of the device. The counter electrode may thus comprises materials selected from material selected from Pt, Au, Ni, Cu, Ag, In, Ru, Pd, Rh, Ir, Os, C, conductive polymer and a combination of two or more of the aforementioned, for example. Conductive polymers may be selected from polymers comprising polyaniline, polypyrrole, polythiophene, polybenzene and acetylene, for example.

Figure 3:
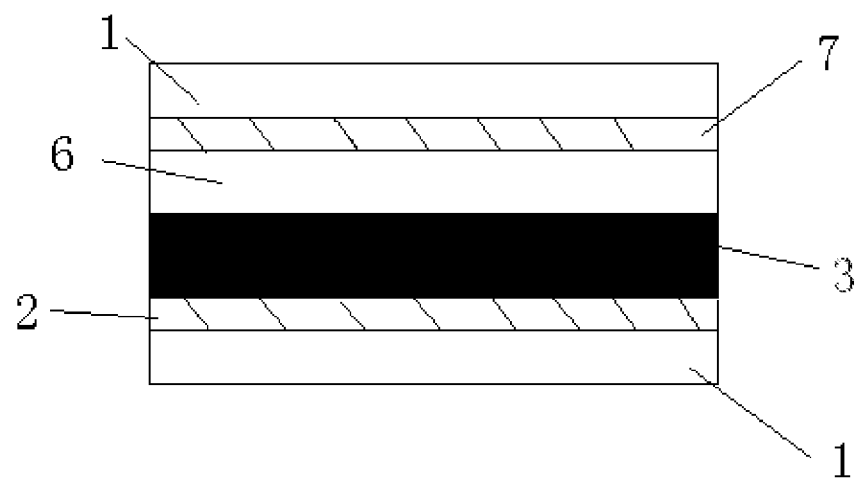
FIG. 3 is a schematic representation of a DSC according to the invention.
Figure 4:
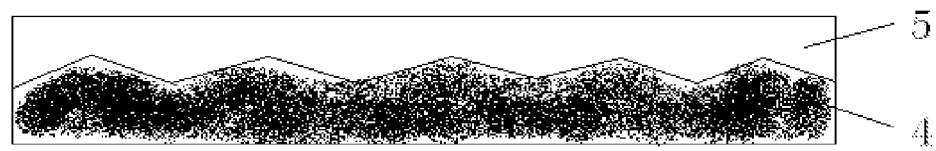
FIG. 4 is a schematic representation of the said light adsorption layer 3, in which 4 indicates a semiconductor nanoparticle layer and 5 indicates a dye layer.

In FIG. 3, the second conductive layer can be considered as part of the counter electrode 7 or as part of the substrate 1 on the top of the device, and is thus not separately shown. If the second conductive layer is considered to be part of the substrate 1, such substrate could be plastic or glass coated with ITO or other materials, as mentioned above, for example.

In FIG. 3, layer 3 is a light absorption layer, which comprises actually at least two separate layers, namely a porous semiconductor layer 4 and, absorbed thereon, a layer of sensitising dyes 5. The porous semiconductor layer may be produced by processes described in the art (B. O'Reagan and M. Grätzel, Nature, 1991, 353, 373) from semiconductor nanoparticles, in particular nanocrystalline particles. Such particles generally have a mean diameter of about 0-50 nm, for example 5-50 nm. Such nanoparticles may be made from a material selected from the group of Si, $TiO_2$, $SnO_2$, ZnO, $WO_3$, $Nb_2O_5$ and $TiSrO_3$, for example. The constitution of the porous layers from nanocrystalline particles is clearly visible in the schematic FIG. 5, showing an embodiment of a flexible cell according to the invention.

The dye layer 5 comprises, besides optional co-adsorbed compounds, such as those disclosed in WO2004/097871A1, for example, at least one dye or sensitizer, or a combination of two or more different sensitizers. For example, the dye may be an organo-metallic compound. Examples for organometallic compounds encompass ruthenium dyes, as they are currently used in such devices. Suitable ruthenium dyes are disclosed, for example, in WO2006/010290.

The dye layer may comprise organic sensitizers. For example, the device may be free of any sensitizer using ruthenium or another noble metal. According to a preferred embodiment of the present invention, the photoelectric conversion device comprises the organic sensitizers of the present invention, in particular an organic compound of formula (1), for example a compound of any one of formula (I)-(X).

The device of the present invention has a layer 6 having the general purpose of mediating the regeneration of electrons in the dye, which were removed due to radiation. These electrons are provided by the counter electrode 7, and layer 6 thus mediates the transport of electrons from the counter electrode to the dye, or of holes from the dye to the counter electrode. The transport of electrons and/or holes may be mediated by electrically conductive materials as such and/or by diffusion of charged molecules having a suitable redox potential. Accordingly, the layer 6 may be an electrolyte layer and/or an electrically conductive charge transport layer.

According to a preferred embodiment of the invention, this intermediate layer 6 is substantially free of a solvent. This embodiment is particularly relevant with respect to flexible devices. Substantially free means, for the purpose of the present invention, that the layer comprises less than 10% by weight, more preferably less than 5wt. %, even more preferably less than 1% and most none added solvent at all. In contrary to many prior art devices and in particular to flexible devices made from polymers, the fact that the intermediate layer is solvent free provides the important advantage that there is no degradation due to solvent evaporation through the one or two substrate layer(s) 1.

According to an embodiment, the solvent-free layer is an electrolyte layer comprising one or more ionic liquids and, optionally additives designed to improve stability and/or the performance characteristics of the device, such as N-alkylbenzimidazole, wherein the alkyl is a C1-C10 alkyl, which may be halogenated, for example.

Electrolytes comprising as a major component ionic liquids (ionic-liquid based electrolytes) are, disclosed, for example, in WO2007/093961, where, in Example 1 a binary electrolyte A is prepared of 0.2 M $I_2$, 0.5 M NMBI (N-Methylbenzimidazole) and 0.1 M guanidinium thiocyanate (GuNCS) in a mixture of PMII (1-methyl-3-propylimidazolium) iodide and EMITCB (1-ethyl-3-methylimidazolium tetracyanoborate), volume ratio: 13:7).

Yu Bai et al. "High-performance dye-sensitized solar cells based on solvent free electrolytes produced from eutectic melts", Nature materials, Vol. 7, August 2008, 626-629, disclose various mixtures of ionic liquids to obtain a composition of ionic liquids having a melting point below room temperature (25° C.). In particular, various combinations of 1-hexyl-3-methylimidazolium iodide (HMII); 1-butyl-3-methylimidazolium iodide (BMII); 1-propyl-3-methyimidazolium iodide (PMII); 1-ethyl-3-methylimidazolium iodide (EMII); 1,3-dimethylimidazolium iodide (DMII); 1-allyl-3-methylimidazolium iodide (AMII) were prepared. In particular, solvent free melts DMII/EMII/AMII/I$_2$ (v:v: 8:8:8:1) and DMII/EMII/EMITCB/I$_2$ (12:12:16:1.67) were successfully used as electrolyte systems in dye-sensitized solar cells.

Furthermore, similar ionic liquid-based electrolyte systems as claimed and disclosed in the international patent application PCT/IB2008/055507, filed on Dec. 23, 2008, are also encompassed by the present invention.

The layer 6 may also be an electrically conductive charge transport layer, in which electrons and/or holes move by electronic motion, instead of diffusion of charged molecules. Such electrically conductive layers are preferably based on organic compounds, including polymers. Accordingly, layer 6 may be an electron and/or hole conducting material. U. Bach et al. "Solid-state dye-sensitized mesoporous TiO$_2$ solar cells with high photon-to-electron conversion efficiencies", Nature, Vol. 395, Oct. 8, 1998, 583-585, disclose the amorphous organic hole transport material 2,2',7,7'-tetrakis(N,N-di-p-methoxyphenyl-amine)9,9'-spirofluorene (OMeTAD) in dye-sensitised solar cells. In WO2007/107961, charge transporting materials, which are liquid at room temperature and their application in dye-sensitized solar cells are disclosed. These materials may be used, for example, for the purpose of the present invention.

Both, said electrolyte layer or charge transport layer may comprise additives for improving the performance of the device, such as dopants in the case of organic charge transporters, and the like.

Some further, preferred embodiments of photoelectric conversion devices are disclosed below.

According to an embodiment, the device of the present invention comprises at least one substrate layer 1, a conductive layer 2, a light absorption layer 3, an intermediate layer 6, and a counter electrode 7, wherein said conductive layer 2, said light absorption layer 3, said intermediate layer 6 and said counter electrode 7 are connected in series. Preferably, the device comprises two transparent substrates 1, on the top and the bottom of the device, respectively. The top of the device corresponds to the top of the drawing in FIG. 3. The top corresponds to the side where the major part of light enters the device. The intermediate layer 6 is an electrolyte layer, provided between the dye layer 5 and the counter electrode 7.

According to another embodiment, the device of the present invention is a flexible device. Preferably, according to this embodiment, the device comprises a flexible substrate 1, a counter electrode 7, a solvent-free electrolyte or charge transport layer 6, a dye layer 5, which may comprise organometallic dyes, organic dyes, or both, a porous semiconductor layer 4, and a conductive layer 2. Preferably, said layers are connected in series, for example in that order from the top to bottom.

Preferably, in the flexible device, the said conductive layer 2 is provided by a conductive metal foil, such as a titanium or zinc foil, as shown by reference numeral 2 in FIG. 5, for example, and said flexible substrate 1 is a polymer or plastic foil. A second conductive layer, which is transparent, is part of the counter electrode 7 and is in contact with the plastic foil as described above (for example in the form of ITO-PET or ITO-PEN). Conductive titanium foils and conductive plastic substrates are disclosed by Seigo Ito et al. Chem. Comm. 2006, 4004-4006, and in EP1095387, for example.

According to an embodiment, the flexible device of the present invention is an inversed solar cell, with electromagnetic radiation entering the cell mainly from the side of the counter electrode (back illumination), as shown in FIG. 5, where the arrow hv refers to the side of illumination.

According to an embodiment, the flexible cell of the present invention is an inversed solar cell, in which, a transparent plastic substrate 1 comprises a counter electrode assembly 7, which, in this order from top to the bottom, comprises a transparent conductive oxide, for example ITO (tin-doped indium oxide) deposited on the flexible plastic foil 1, and a catalyst, such as carbon or Pt (platinum), for example.

On the bottom end, a conductive foil 2, preferably a metal foil, such as a Ti or zinc foil, for example, is provided, which may but need not be provided on a flexible support, such as a plastic material.

The present invention provides a method for synthesising the organic dyes of the invention. The synthesis route is generally illustrated by Scheme 1 provided below:

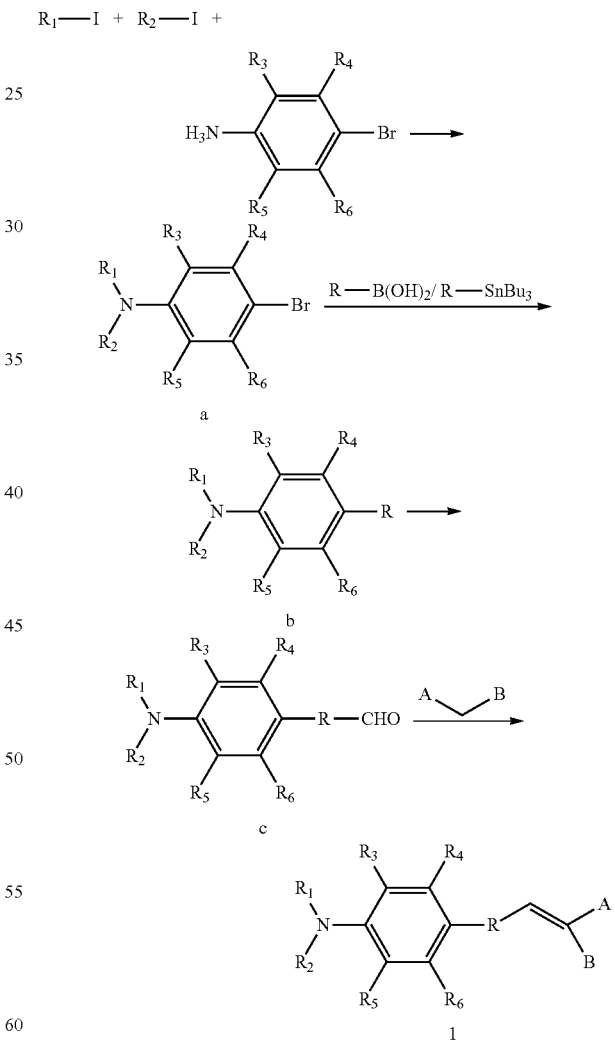

Synthesis of Compound a

R$_1$I, R$_2$I, substituted-4-bromoaniline, and toluene are mixed, preferably with a mol ratio of 1:1:1:1. The reaction mixture is heated, for example to 120° C. and refluxed, for example for about 24 hours under protected atmosphere, such as under Ar. Then water can be added and the mixture may be cooled down to room temperature and extracted with chloroform, for example. The organic phase is preferably washed, for example with water, for example three times, and dried, for example over anhydrous sodium sulfate. After removing the solvent, the residue is purified, for example by column chromatography to give compound a.

The referred $R_1$ and $R_2$ may be selected, independently one from the other, from hydrogen atom (H), alkyl, alkoxyl, aromatic hydrocarbons, or heterocycles and derivatives these, wherein said alkyl, alkoxyl, aromatic hydrocarbon or heterocycle may be substituted or unsubstituted and may contain one or more heteroatoms. According to a preferred embodiment, $R_1$ and $R_2$ are identical. According to a preferred embodiment, $R_1$ and $R_2$ are one of the groups of H, alkyl, aromatic hydrocarbon, alkyoxy or heterocycles and their derivatives.

Synthesis of Compound b

The obtained compound a, for example as depicted above, tetrakis (triphenylphosphine) palladium, potassium carbonate aqueous solution and $RB(OH)_2$ or $RSnBu_3$ may be mixed with molar ratio 1:1:0.8:0.1, for example, and dissolved in THF (a:THF, 1:500 mole ratio, for example). The reaction mixture is preferably heated, for example to 70° C. and the reaction is preferably performed for about 24 hours under protective conditions, for example under Ar. Then the mixture is preferably cooled down, preferably to room temperature (25° C.) and extracted. The organic phase may be washed with sodium carbonate aqueous solution and water three times, for example, and dried over anhydrous sodium sulfate. After removing solvent, the residue was purified by column chromatography, for example, to give compound b shown of Scheme 1.

Synthesis of Compound c

The obtained compound b, anhydrous DMF and 1,2-dichloroethane may be mixed, for example with a molar ratio of about 1:10:400. After cooling the mixture, preferably to about 0° C., phosphorus oxychloride is preferably added dropwise into the mixture (compound b:phosphorus oxychloride, 1:1.2 mol ratio, for example) under inert gases, for example. Then the reaction mixture is preferably heated to about 84° C. and refluxed for 4 hours, for example. Water is preferably added into the mixture, followed by neutralizing, for example with sodium acetate. The mixture is preferably extracted, for example with chloroform. Then the organic phase may be dried. After removing the solvent, the residue may be purified, for example by column chromatography, to yield compound c.

Synthesis of the Organic Dyes Represented by Formula (1):

Compound c obtained according to the general procedure above, $ACH_2B$, piperidine, and acetonitrile are preferably mixed, for example with a molar ratio of about 1:1.1:10:600. The reaction mixture is preferably heated to 82° C., refluxed, for example for 6 hours under protective atmosphere, such as Ar, for example, and is then preferably cooled down to about room temperature (25° C.). Then, acetonitrile is preferably evaporated was evaporated, and water is preferably added into the mixture. The solution is preferably acidified with HCl to pH 1-2 and may then be extracted, for example with dichloromethane. Then the organic phase is preferably dried. After removing the solvent, the residue may be purified, for example by column chromatography to give the organic dye represented by formula (1).

The present invention also relates to the fabrication of a photoelectric conversion device, for example those comprising the organic dye of the present invention, or flexible devices as defined herein. Exemplary steps and conditions of the fabrication are shown as following:

The fabrication procedure for nanocrystalline $TiO_2$ particles and photoanode with double layer of $TiO_2$ nanoparticles has been reported. (Wang P. et al., Enhance the Performance of Dye-Sensitized Solar Cells by Co-grafting Amphiphilic Sensitizer and Hexadecylmalonic Acid on $TiO_2$ Nanocrystals, J. Phys. Chem. B., 107, 2003, 14336).

The prepared $TiO_2$ electrodes are preferably immersed into a solution containing a sensitizer dye, for example the one represented by formula (1) and, for example, a co-adsorbent, for several hours. The surface coverage of the sensitizer on $TiO_2$ particles is preferably more than 80%, preferably more than 90%.

The double layer nanocrystalline $TiO_2$ film electrode may be assembled with a thermally platinized conducting glass electrode. Of course, in flexible devices, an alternative procedure is preferably used (Seigo et al.). The two electrodes may be separated by a 10-50 μm thick hot-melt ring and sealed up by heating. The internal space is preferably filled with an electrolyte or a liquid hole conductor material. After that, the injection hole is preferably sealed. A detail method is disclosed in the reference of Wang P. et al. (A Solvent-Free, $SeCN^-/(SeCN)_3^-$ Based Ionic Liquid Electrolyte for High-Efficiency Dye-Sensitized Nanocrystalline Solar Cell, J. Am. Chem. Soc., 126, 2004 7164).

For example, the devices may be manufactured according to the general fabrication procedure reported by Wang P. et al., "Enhance the Performance of Dye-Sensitized Solar Cells by Co-grafting Amphiphilic Sensitizer and Hexadecylmalonic Acid on $TiO_2$ Nanocrystals", J. Phys. Chem. B., 107, 2003, 14336.

The invention is illustrated by the Examples below, which are not intended to limit the scope of the invention.

EXAMPLES

Example 1

The Synthesis of Organic Dye I

Synthesis of Compound a (in the Scheme Below):

2-[N, N-bis(9,9-dimethylfluoren-2yl)-4-bromoaniline (0.256 g, 0.46 mmol), (thieno[3,2-b]thiophen-2-yl)boronic acid (0.1 g, 0.51 mmol), and tetrakis(triphenylphosphine) palladium (0.058 g, 0.051 mmol) were dissolved in the mixture of THF (17 ml) and 2 mol/L potassium carbonate aqueous solution (1.7 ml) in a flask (volume, 50 mL). The mixture was heated to 70° C. and the reaction was performed for 24 hours under Ar. Then the mixture was cooled down to room temperature and extracted with chloroform. The organic phase was washed with sodium carbonate aqueous solution and $H_2O$ three times, and subsequently dried over anhydrous sodium sulfate. After removing solvent, the residue was purified by column chromatography with toluene/hexane (1/5, v/v) as eluent to give a yellow solid a. Yield: 86%.

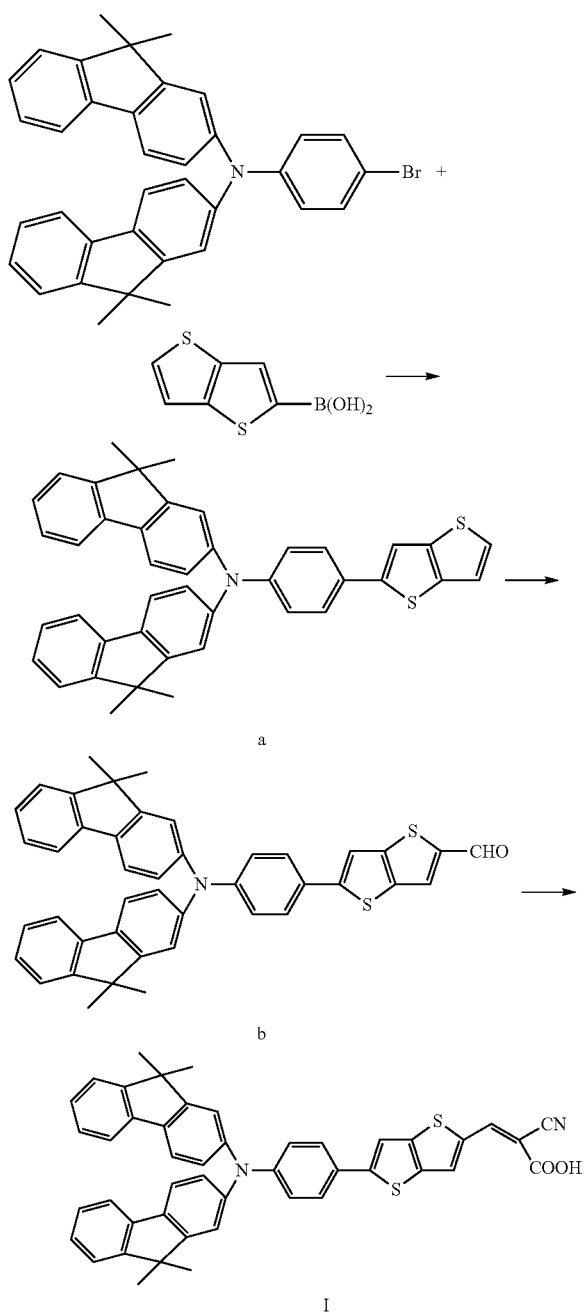

Synthesis of b:
Compound a obtained above (0.286 g, 0.465 mmol) was dissolved in dichloromethane (1.2 ml), followed by adding anhydrous DMF (0.36 ml). After cooling the mixture to 0° C., phosphorus oxychloride (51.1 μL, 0.558 mmol) was added by dropwise under Ar. The reaction mixture was heated to 84° C. and refluxed for 4 hours. Water was added into the reaction mixture, followed by neutralizing with sodium acetate. The mixture was extracted with chloroform, and the organic phase was dried. After removing the solvent, the residue was purified by column chromatography with toluene/hexane (3:1, v/v) as eluent to give an orange solid b. Yield: 92%.

Synthesis of Organic Dye I:
Compound b obtained above (0.33 g, 0.573 mmol), cyanoacetic acid (0.053 g, 0.624 mmol), acetonitrile (20 ml), and piperidine (0.026 ml, 0.624 mmol) were added in a flask (volume, 50 ml). The reaction mixture was heated to 82° C. and refluxed for 6 hours under Ar. After cooling the mixture to room temperature, acetonitrile was evaporated and water was added. The solution was acidified with HCl to pH 1-2 and extracted with dichloromethane. The organic phase was dried. After removing the solvent, the residue was purified by column chromatography with chloroform as eluent to give the organic dye I. Yield: 93%.

Example 2

DSC Fabricated with Organic Dye I 20-nm-sized $TiO_2$ colloid was printed on the fluorine-doped $SnO_2$ conducting glass, heated to 400° C. and sintered for 12 hours. The thickness of 20 nm sized $TiO_2$ particles is 7 μm. With the same method, a second layer of 400 nm sized light scattering anatase particles (thickness 5 μm) was further coated to make a double layer film. Fabrication procedure for nanocrystalline $TiO_2$ particles and photoanode with double layer of $TiO_2$ nanoparticles has been reported. (reference: Wang P. et al., Enhance the Performance of Dye-Sensitized Solar Cells by Co-grafting Amphiphilic Sensitizer and Hexadecylmalonic Acid on $TiO_2$ Nanocrystals, J. Phys. Chem. B., 107, 2003, 14336).

The prepared $TiO_2$ electrodes were immersed into a solution containing 300 μM dye represented by formula (I) and 10 mM Chenodeoxycholic acid (3,7-dihyroxy-5-cholic acid) in chlorobenzene for 12 hours. The surface coverage of the sensitizer on $TiO_2$ particles is more than 90%. The double layer nanocrystalline $TiO_2$ film electrode was assembled with thermally platinized conducting glass electrode. The two electrodes were separated by a 35 μm thick hot-melt ring and sealed up by heating. The internal space was filled with an electrolyte consisting of: 1.0 M 1,3-dimethylimidazolium iodide, 0.05 M LiI, 0.1 M guanidinium thiocyanate, 30 mM $I_2$, 0.5 M tert-butylpyridine in the mixture of the solvents acetonitrile and valeronitrile (85/15, v/v). After that, the electrolyte-injection hole was sealed. For the fabrication details see the reference of Wang P. et al., "A Solvent-Free, $SeCN^-$/$(SeCN)_3^-$ Based Ionic Liquid Electrolyte for High-Efficiency Dye-Sensitized Nanocrystalline Solar Cell", J. Am. Chem. Soc., 126, 2004, 7164.

Device characteristics were determined under AM 1.5 full sunlight (100 mw/cm²). The short circuit photocurrent density ($I_{sc}$), open circuit photovoltage ($V_{oc}$), and fill factor (ff) are 13.35 mA/cm², 776.6 mV, and 0.749, respectively, yielding an overall conversion efficiency 7.8%.

Example 3

Synthesis of Organic Dye II and DSC Containing the Dye

The synthesis of organic dye II was performed according to the procedure and condition for organic dye I in Example 1, except that thieno[3,2-b]thiophene was replaced with dithieno[3,2-b;2',3'-d]thiophene. DSC was fabricated according to the method of Example 2, except that dye I was replaced with dye II. The obtained cell parameters are shown in the Table 1.

Example 4

Synthesis of Organic Dye III and DSC Containing the Dye

The synthesis of organic dye III was performed according to the same procedure and under the same conditions as disclosed for organic dye I in Example 1, except that thieno[3,2-b]thiophene was replaced with thiophenefluorene. The DSC was fabricated according to the method of Example 2, except that organic dye I was replaced with organic dye III. The obtained cell parameters are shown in the Table 1.

Example 5

Synthesis of Organic Dye IV and DSC Containing the Dye

Scheme of Synthesis:

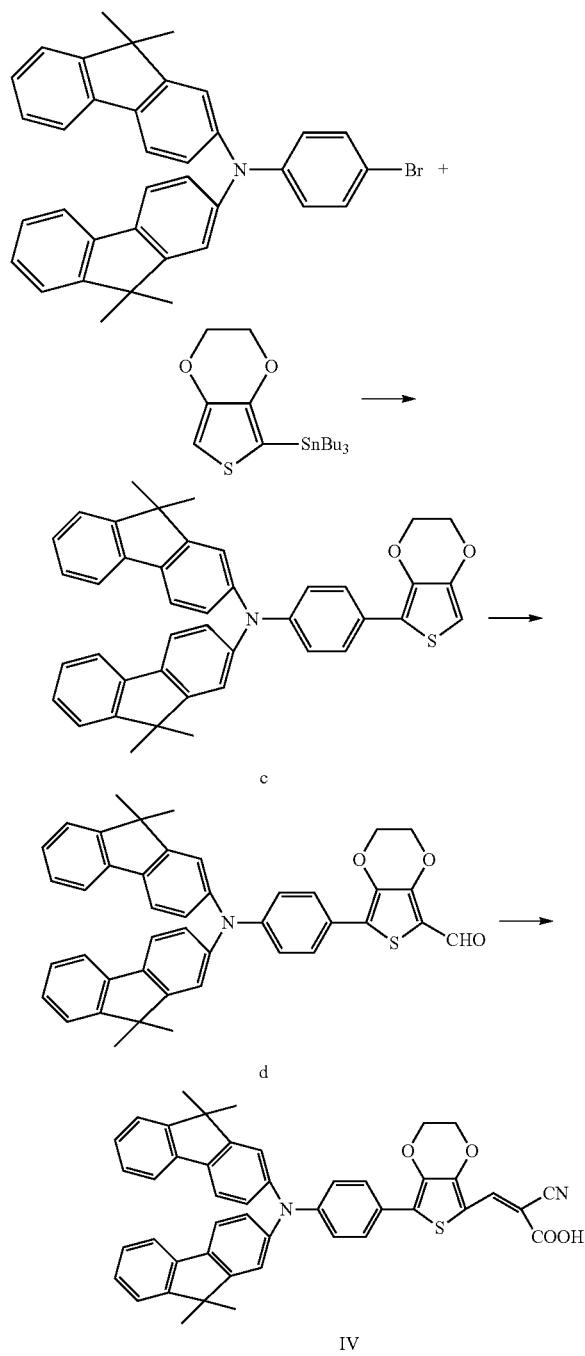

Synthesis of c:

Tributyltin ethylene dioxythiophene (0.7 g, 1.62 mmol) and 2-[N, N-bis(9,9-dimethylfluoren-2yl)-4-bromoaniline (0.6 g, 1.08 mmol) were dissolved in 45 ml toluene, followed by adding bis(triphenyl phosphate) palladium dichloride (0.084 g, 0.119 mmol) and tetrakis(triphenylphosphine)palladium (0.14 g, 0.119 mmol). The reaction mixture was heated to 115° C. and refluxed under Ar. Water was added to the mixture. After cooling to room temperature, the mixture was extracted with toluene. The organic phase was dried. After removing the solvent, the residue was purified by column chromatography to give c.

Synthesis of d:

The obtained c (0.25 g, 0.405 mmol) was dissolved in 20 ml 1,2-dichloroethane, followed by adding DMF (0.32 ml, 4.05 mmol). After cooling the mixture to 0° C., phosphoryl chloride (0.045 ml, 0.486 mmol) was added and the reaction was performed for 1 hour. After heating the mixture to room temperature, the reaction was further performed for 5 hours. Then 20 ml sodium acetate was added. The mixture was stirred for 30 min at room temperature, followed by being extracted with dichloromethane. The organic phase was dried. After removing the solvent, d was obtained.

Synthesis of Organic Dye IV:

The obtained d (0.28 g, 0.43 mmol) was dissolved in 60 ml acetonitrile, followed by adding piperidine (0.02 ml, 0.22 mmol) and cyanoacetic acid (0.044 g, 0.52 mmol). The reaction mixture was heated to 82° C. and refluxed for 24 hours under Ar. Water was added. The solution was acidified with HCl to pH 1-2 and extracted with dichloromethane. The organic phase was dried. After removing the solvent, the residue was loaded onto silica gel with chloroform as eluent to give organic dye IV.

According the method of Example 2, a DSC was fabricated except that organic dye I was replaced with organic dye IV. The obtained cell parameters are shown in the Table 1.

Example 6

Synthesis of Organic Dye V and DSC Containing the Dye

The synthesis of organic dye V was performed according to the procedure and under the conditions described for organic dye IV in Example 5, except that ethylenedioxythiophene was replaced with thieno[3,2-b]thiophene-thieno[3,2-b]thiophene. A DSC was fabricated according to the method of Example 2, except that organic dye I was replaced with organic dye V. The obtained cell parameters are shown in Table 1.

Example 7

Synthesis of Organic Dye VI and DSC Containing the Dye

The synthesis of organic dye VI was performed according to the procedure and under the conditions described for organic dye IV in Example 5 except that ethylenedioxythiophene was replaced with thieno[3,2-b]thiophene-dithieno[3,2-b;2',3'-d]thiophene. The DSC was fabricated according to the method of Example 2, except that organic dye I was replaced with organic dye VI. The obtained cell parameters are shown in the Table 1 below.

Example 8

Synthesis of Organic Dye VII and DSC with the Dye

The synthesis of organic dye VII was performed according to the procedure and under the conditions described for organic dye IV in Example 5, except that ethylenedioxythiophene was replaced with ethylenedioxythiophene-ethylenedioxythieno[3,2-b]thiophene. A DSC was fabricated according to the method of Example 2, except that organic dye I was replaced with organic dye VII. The obtained cell parameters are shown in Table 1.

Example 9

Synthesis of Organic Dye VIII and DSC Comprising the Dye

The synthesis of organic dye VIII was performed according to the procedure and under the conditions described for organic dye IV in Example 5, except that ethylenedioxythiophene was replaced with ethylenedioxythiophene-thiophenefluorene. A DSC was fabricated according to the method of Example 2 except that organic dye I was replaced with organic dye VIII. The obtained cell parameters are shown in Table 1.

Example 10

Synthesis of Organic Dye IX and DSC Comprising the Dye

The synthesis of organic dye IX was performed according to the procedure and under the conditions described for organic dye IV in Example 5, except that ethylenedioxythiophene was replaced with ethylenedioxythiophene-thieno[3,2-b]thiophene-ethylenedioxythiophene. A DSC was fabricated according to the method of Example 2, except that organic dye I was replaced with organic dye IX. The obtained cell parameters are shown in Table 1.

Example 11

Synthesis of Organic Dye X and DSC Comprising the Dye

The synthesis of organic dye X shown above was performed according to the procedure and condition for organic dye IV in Example 5, except that ethylenedioxythiophene was replaced with ethylenedioxythiophene-thieno[3,2-b]thiophene-dithieno[3,2-b;2',3'-d]thiophene. A DSC was fabricated according to the method of Example 2, except that organic dye I was replaced with organic dye X. The obtained cell parameters are shown in Table 1 below.

TABLE 1

Photovoltaic parameters of DSCs with organic dyes of the invention

| Dye formula | Open circuit voltage (mV) | Short circuit current density (mA/cm$^2$) | Fill factor ff | Efficiency (%) |
|---|---|---|---|---|
| I | 776.6 | 13.35 | 0.749 | 7.8 |
| II | 778.2 | 13.98 | 0.726 | 8.4 |
| III | 773.6 | 12.66 | 0.784 | 8.0 |
| IV | 780.3 | 14.65 | 0.731 | 8.5 |
| V | 772.1 | 15.93 | 0.719 | 9.6 |

TABLE 1-continued

Photovoltaic parameters of DSCs with organic dyes of the invention

| Dye formula | Open circuit voltage (mV) | Short circuit current density (mA/cm$^2$) | Fill factor ff | Efficiency (%) |
|---|---|---|---|---|
| VI | 782.9 | 14.84 | 0.734 | 8.7 |
| VII | 777.9 | 14.55 | 0.744 | 8.8 |
| VIII | 774.7 | 16.70 | 0.711 | 9.9 |
| IX | 765.2 | 16.54 | 0.738 | 9.7 |
| X | 779.8 | 16.78 | 0.712 | 10.2 |

Example 12

Preparation of a Flexible Solar Cell with Solvent-Free Electrolyte Layer

A flexible dye-sensitized solar cell with a Ti-metal substrate is prepared according to the procedure disclosed by Seigo Ito et al., Chem. Commun. 2006, 4004-4006, using the N-719 sensitizer dye, and a Pt catalyst coated on ITO/PEN (polyethylene naphthalate) as counter electrode on a plastic substrate as described in this publication.

A drop of a solvent free electrolyte consisting of 0.2 M $I_2$, 0.5 M NMBI (N-Methylbenzimidazole) and 0.1 M guanidinium thiocyanate (GuNCS) in a mixture of PMII (1-methyl-3-propylimidazolium) iodide and EMIB(CN)$_4$ (volume ratio: 13:7), is put on a hole in the back of the working electrode, and introduced in the cell via vacuum backfilling, followed by sealing with a Surlyn layer.

In this way, a functioning flexible solar cell with power conversion efficiency in the range of 4-7% is obtained.

Example 13

Preparation of a Flexible Solar Cell with Solvent-Free Electrolyte Based on Ionic Liquids The same procedure as in Example 12 is followed, but the electrolyte was replaced by an electrolyte with the following components:

1,3-dimethylimidazolium iodide (DMII);
1-ethyl-3-methylimidazolium iodide (EMII);
1-ethyl-3-methylimidazolium tetracyanoborate (EMITCB);
iodine ($I_2$);
N-butylbenzoimidazole (NBB, base);
guanidinium thiocyanate (additive).

These components were added in a mol ratio of in the mol ratio 12:12:16:1.67:3.33:0.67.

Again, a functioning flexible solar cell with power conversion efficiency in the range of 4-7% is obtained.

Example 14

Preparation of a Flexible Solar Cell with Solvent-Free Hole Conductor

The hole conducting material tris(p-methoxyethoxyphenyl)amine (TMEPA) was synthesized as disclosed in Example 1 of WO2007/107961. For use in the solar cells, TMEPA was doped with 0.07 M N(PhBr)$_3$ SbCl$_6$ as electrochemical dopant, had the addition of 12 µl of tertbutylpyridine to every 100 µl of TMEPA and 0.1 M of Li[(CF$_3$SO$_2$)$_2$N]. These additives were pre-dissolved in acetonitrile before incorporation with the liquid hole-transporter. The prepared "solutions" were pumped down to $10^{-1}$ mbar overnight, in order to remove all residual solvent before device fabrication. The doped organic hole conducting material is liquid at room temperature and is introduced in the same manner through a hole into pre-prepared devices as disclosed in Example 12 and 13. In this way, a flexible device based on a electrically conductive hole transporting material with a conversion efficiency of about 1-2% is obtained.

Examples 15-17

Flexible Solar Cells with Organic Dyes

Examples 12-14 were repeated, but dye X disclosed in Example 11 was used instead of the ruthenium dye N-719 used by Seigo Ito et al. In this way, flexible solar cells with organic dyes are obtained, having power conversion efficiencies well above about 1%, and in some even above about 5%.

In the flexible cells of Examples 12-17, the stability problem of electrolyte degradation due to solvent evaporation is not observed.

The invention claimed is:
1. An organic dye of formula (1):

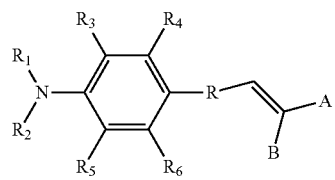

(1)

wherein:
 $R_1$ and $R_2$ are selected independently from substituted aryls, the substituents being selected from alkyl, alkoxyl, aryl, arylated alkyl, alkylated aryl, and alkoxylated aryl;
 $R_3$, $R_4$, $R_5$ and $R_6$ are, independently one from the other, selected from a hydrogen atom (H), alkyl, alkoxyl, aromatic hydrocarbons, or heterocycles, wherein said alkyl, alkoxyl, aromatic hydrocarbon or heterocycle are unsubstituted and wherein one; or more of $R_3$, $R_4$, $R_5$ and $R_6$ can also be a halogen;
 R consists of 2 to 10 moieties, wherein said moieties are independently selected from the moieties of formulae (2)-(21) below and wherein any moiety of R selected from the moieties (2)-(21) succeeds to a different moiety selected from the moieties (2)-(21):

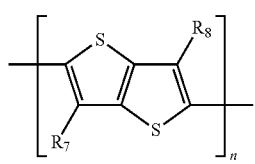

(2)

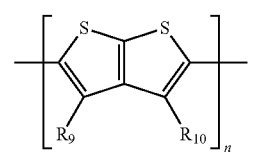

(3)

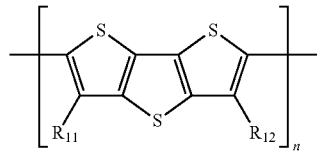

(4)

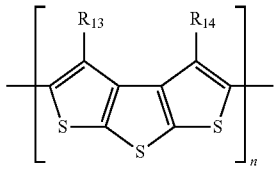

(5)

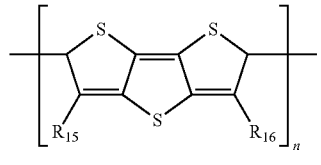

(6)

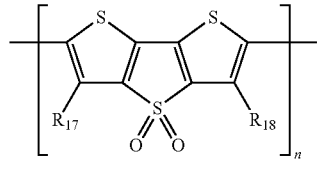

(7)

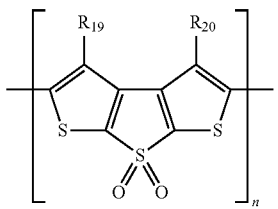

(8)

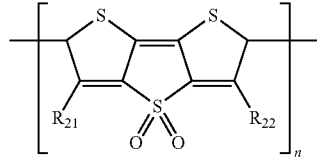

(9)

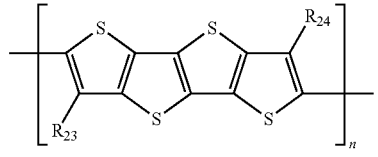

(10)

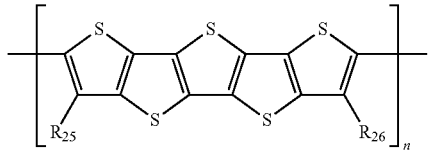

(11)

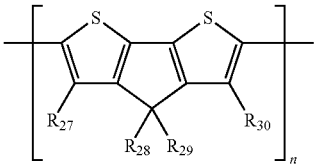

(12)

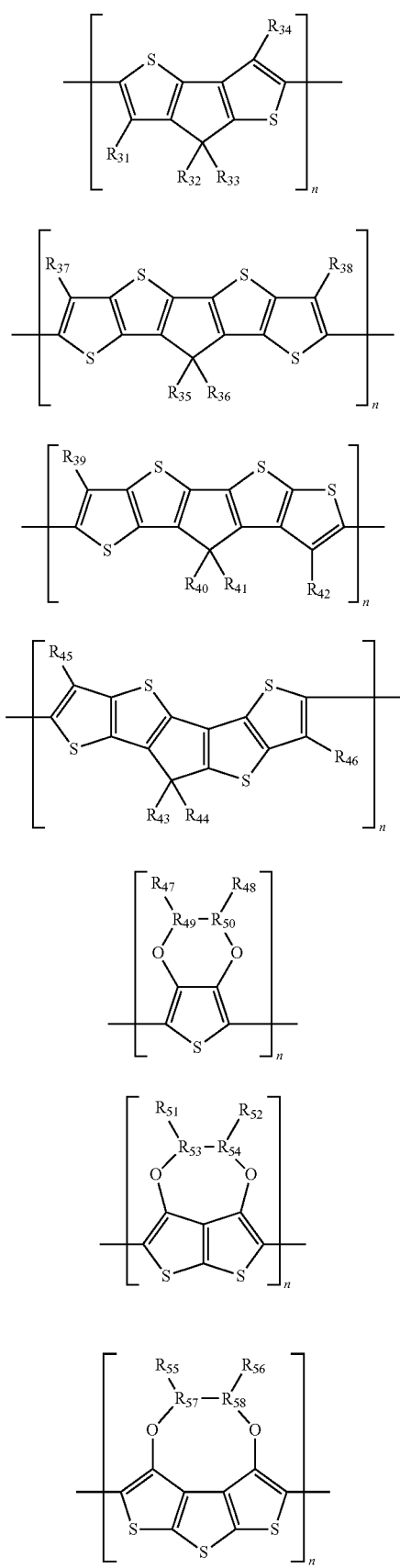

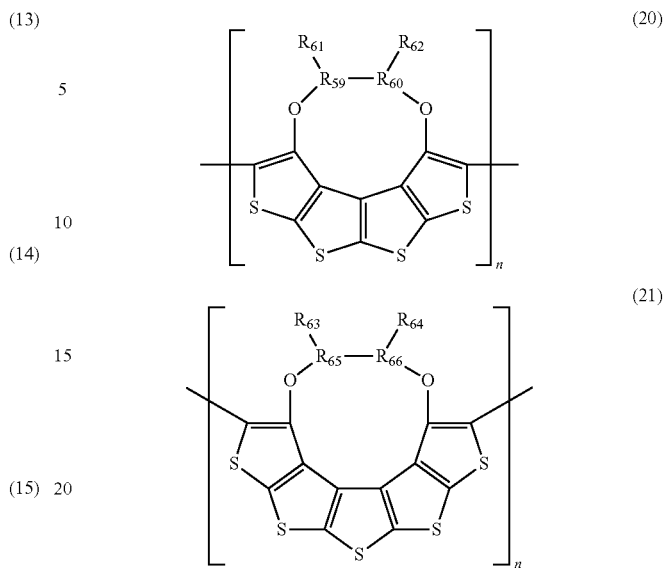

wherein:

n is an integer selected from 1;

$R_{49}$, $R_{50}$, $R_{53}$, $R_{54}$, $R_{57}$, $R_{58}$, $R_{59}$, $R_{60}$, $R_{65}$, and $R_{66}$ are each a —CH moiety;

$R_7$ to $R_{66}$, with the exception of $R_{49}$, $R_{50}$, $R_{53}$, $R_{54}$, $R_{57}$, $R_{58}$, $R_{59}$, $R_{60}$, $R_{65}$, $R_{66}$, are selected, independently one from the others, from H, hydroxyl, nitryl, amido, acyl, alkyl, cycloalkyl, alkoxyl, aromatic hydrocarbons, alkylsulfonyl, alkylthio, ester group, alkyl halide, halogen, sulfonyl, cyano, alkenyl, acyloxyl, carboxyl and heterocycles;

A in the compound of formula (1) is an acceptor group selected from cyano, group, acyl, group, aldehyde group, carboxyl group, acylamine group (—C(O)NH$_2$), sulfonic acid group (—S(O)$_2$OH), nitryl group, and quaternary ammonium group;

B is selected from carboxyl group, phosphorus acid group (—P(O)(OH$_2$), sulfonic acid group (—S(O)$_2$OH), hypophosphorous acid group (—P(O)(OH), hydroxyl group, carboxylic acid group, boric acid group (—OB(OH)$_2$), and squaric acid group (—OC$_4$O$_2$(OH)), including deprotonated forms of the aforementioned.

2. The organic dye of claim 1, wherein one or more of the substituents of $R_1$ and $R_2$ comprise one or more heteroatoms selected from N, O, P or S.

3. The organic dye of claim 2, wherein one or more of the substituents of $R_1$ and $R_2$ are selected from a substituted phenyl or a substituted aromatic system of condensed cycles.

4. The organic dye of claim 1, wherein $R_1$ and $R_2$ are 9,9-dimethlyfluoren-2-yl.

5. The organic dye of claim 1, which is selected from the compounds of any one of formula (VI) to (X) below:

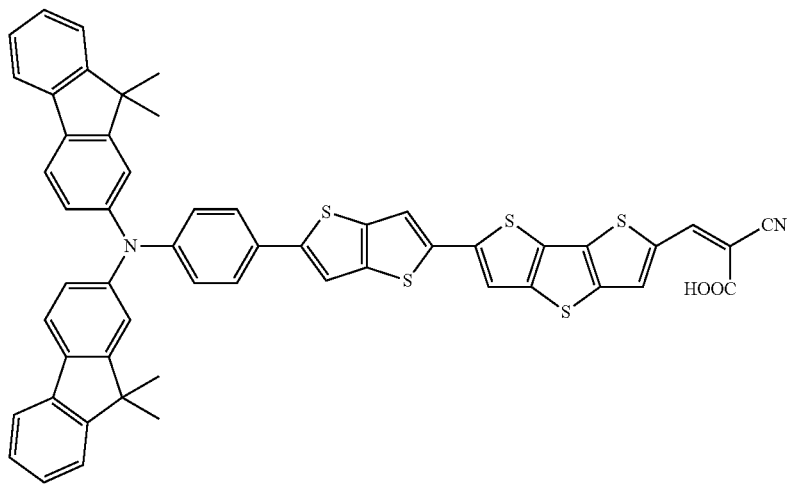
(VI)
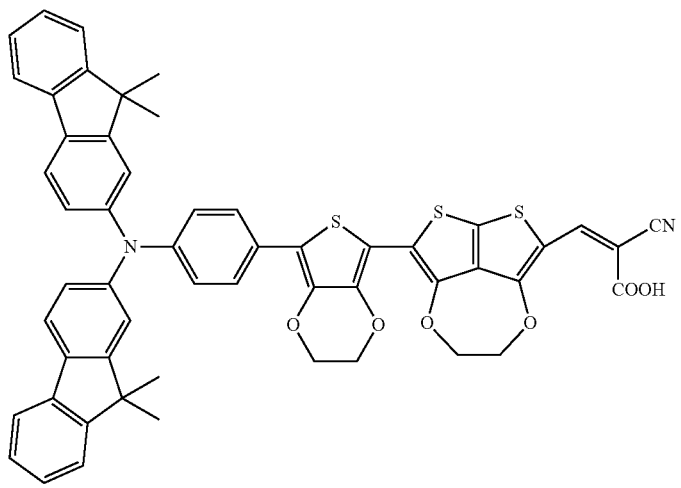
(VII)
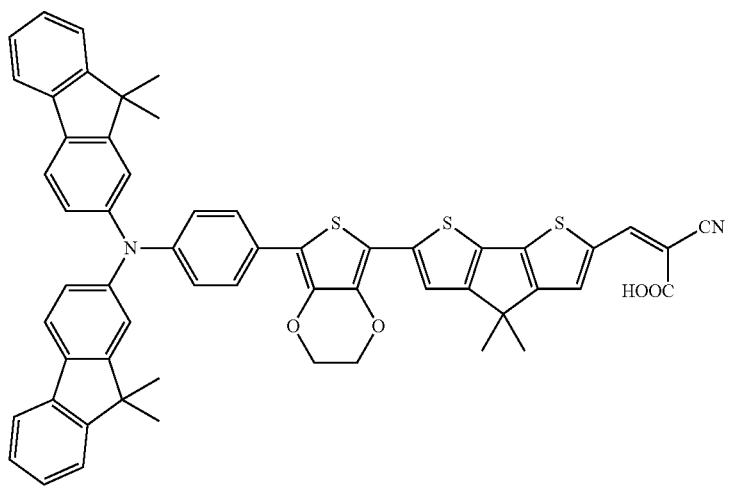
(VIII)

-continued

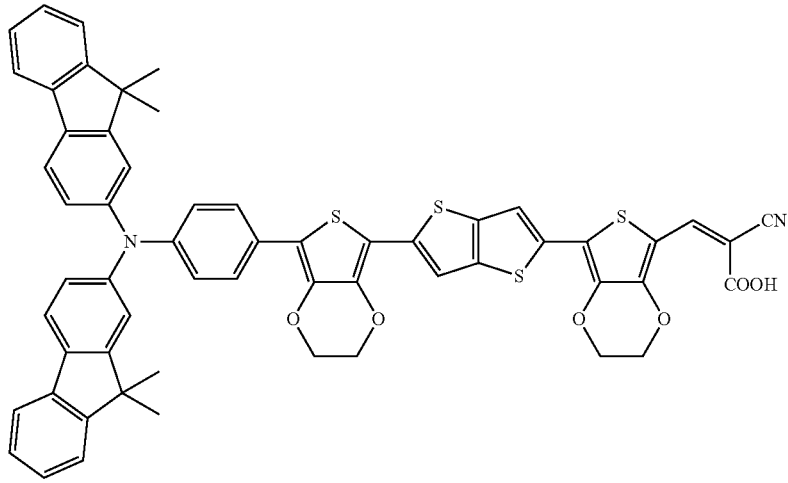

(IX)

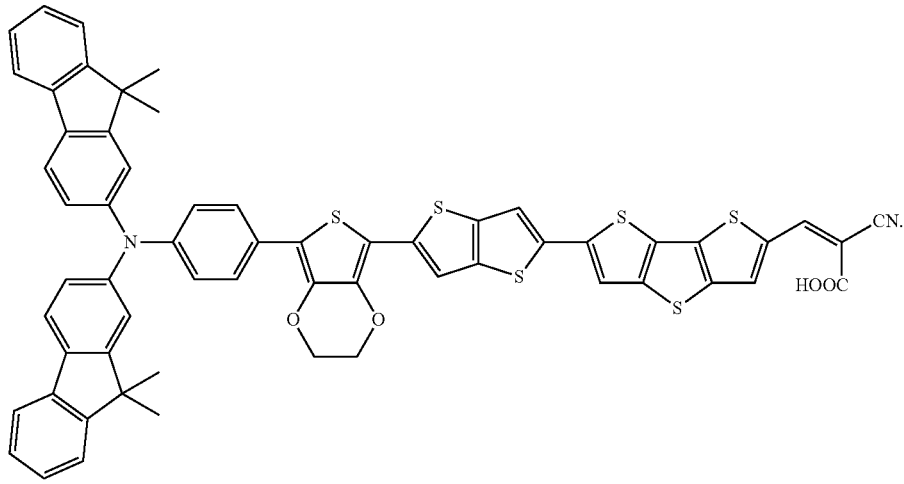

(X)

6. A dye-sensitised solar cell (DSC) comprising an organic dye as in one of claim 1.

7. The dye-sensitised solar cell of claim 6, which comprises an electrically conductive layer (2), an intermediate layer (6) and a light absorption layer (3) comprising a porous semiconductor layer (4) and a dye-sensitizer layer (5), wherein the said porous semiconductor layer (4) is in contact with and on said electrically conductive layer (2), wherein said dye-sensitizer layer (5) is adsorbed on said porous semiconductor layer (4), on the side facing the intermediate layer (6).

8. A photoelectric conversion device comprising: at least one substrate layer (1), a conductive layer (2), a light absorption layer (3), an intermediate layer (6), and a counter electrode (7), wherein said intermediate layer (6) is an electrolyte layer (6) and/or an electrically conductive charge transport layer, which is provided between a dye layer (5) comprising a compound according to claim 1 and said counter electrode (7) and wherein said conductive layer (2), said light absorption layer (3), said intermediate layer (6) and said counter electrode (7) are connected in series.

9. The device of claim 8, which is a flexible solar cell, in which the at least one substrate layer (1) comprises a flexible plastic.

10. The device of claim 8 comprising, in this order from the bottom to the top, a first conductive layer (2), a porous semiconductor layer (4), a dye layer (5), an ion- or charge transport layer (6), a counter electrode layer (7), a second conductive layer, and, a flexible plastic substrate layer (1).

11. The device according to claim 8, wherein said dye layer (5) comprises an organometallic sensitizer compound and/or an organic sensitizer compound.

12. The device of claim 8, wherein the intermediate layer (6) is substantially free of solvent.

13. The device of claim 12, wherein the intermediate layer (6) being free of solvent is an electrolyte layer comprising one or more ionic liquids.

14. The device of claim 8, wherein said at least one substrate layer (1) comprises a plastic selected from the groups of polyethylene terephthalate, polyethylene naphthalate, polycarbonate, polypropylene, polyimide, 3-acetyl cellulose, and polyethersulfone.

15. The device of claim 8, which comprises a flexible transparent substrate layer (1), which is provided on the side of the counter electrode (7).

16. The device of claim 9, which comprises a flexible transparent substrate layer (1) comprising, on a side facing the inside of the cell, a transparent second electrically conductive layer.

17. The device of claim 8, wherein said substrate layer (1) and said second conductive layer are transparent.

18. The device of claim 8, wherein said device comprises a top and/or bottom substrate layer (1), wherein at least one of said substrate layers is transparent.

* * * * *

UNITED STATES PATENT AND TRADEMARK OFFICE
CERTIFICATE OF CORRECTION

PATENT NO. : 8,487,119 B2
APPLICATION NO. : 12/735629
DATED : July 16, 2013
INVENTOR(S) : Mingfei Xu et al.

It is certified that error appears in the above-identified patent and that said Letters Patent is hereby corrected as shown below:

In the Specifications:

Column 4, formula (12) about line 21: "R25" should be replaced by "R27"
Column 20, line 45: "density (Lsc)" should be replaced by "density (Jsc)"

Signed and Sealed this
Tenth Day of September, 2013

Teresa Stanek Rea
*Acting Director of the United States Patent and Trademark Office*